(12) United States Patent
Mimura et al.

(10) Patent No.: US 7,090,647 B2
(45) Date of Patent: Aug. 15, 2006

(54) BEDSORE MAIN-FACTOR MEASURING DEVICE

(75) Inventors: Maki Mimura, Hiroshima (JP); Hidekazu Okazaki, Hiroshima (JP)

(73) Assignee: Molten Corporation, Hiroshima (JP)

( * ) Notice: Subject to any disclaimer, the term of this patent is extended or adjusted under 35 U.S.C. 154(b) by 0 days.

(21) Appl. No.: 10/507,890

(22) PCT Filed: Mar. 24, 2003

(86) PCT No.: PCT/JP03/03514

§ 371 (c)(1),
(2), (4) Date: Sep. 17, 2004

(87) PCT Pub. No.: WO03/079898

PCT Pub. Date: Oct. 2, 2003

(65) Prior Publication Data

US 2005/0148904 A1    Jul. 7, 2005

(30) Foreign Application Priority Data

Mar. 25, 2002 (JP) ............................. 2002-083065

(51) Int. Cl.
*A61B 5/103* (2006.01)
*A61B 5/117* (2006.01)
(52) U.S. Cl. ................................................. 600/587
(58) Field of Classification Search .................. None
See application file for complete search history.

(56) References Cited

U.S. PATENT DOCUMENTS

| | | | | |
|---|---|---|---|---|
| RE32,180 E | * | 6/1986 | Lewiner et al. | 340/573 |
| 4,813,428 A | * | 3/1989 | Muraki et al. | 128/721 |
| 4,987,904 A | * | 1/1991 | Wilson | 128/774 |
| 5,341,687 A | * | 8/1994 | Stan | 73/862.046 |
| 5,461,924 A | * | 10/1995 | Calderara et al. | 73/786 |
| 5,571,973 A | * | 11/1996 | Taylot | 73/862.046 |
| 5,838,244 A | * | 11/1998 | Schmidt et al. | 340/635 |
| 5,911,694 A | * | 6/1999 | Ikeda et al. | 600/587 |
| 6,134,970 A | * | 10/2000 | Kumakawa et al. | 73/730 |
| 6,306,107 B1 | * | 10/2001 | Myklebust et al. | 600/587 |
| 6,681,638 B1 | * | 1/2004 | Kazerooni et al. | 73/760 |
| 2004/0194220 A1 | * | 10/2004 | Price et al. | 5/713 |
| 2005/0076715 A1 | * | 4/2005 | Kuklis et al. | 73/541 |

FOREIGN PATENT DOCUMENTS

| | | |
|---|---|---|
| EP | 1 093 755 | 4/2001 |
| JP | 2000-111420 | 4/2000 |
| JP | 2000-283869 | 10/2000 |

(Continued)

*Primary Examiner*—Max F. Hindenburg
*Assistant Examiner*—Kristin D. Rogers
(74) *Attorney, Agent, or Firm*—Westerman, Hattori, Daniels & Adrian, LLP.

(57) ABSTRACT

A distortion generating sheet (22) intervenes between a first and a second flexible sheets (11) and (12), respectively, with one end (23) thereof fixed to the first sheet (11), and the other end (24) fixed to the second sheet (12). As a consequence, when a shear takes place across the first and second sheets (11) and (12), respectively, the shear is conveyed to the distortion generating sheet (22). A strain gauge (21) fixed to the distortion generating sheet (22) detects and measures the distortion generated by the shear in the distortion generating sheets (22). A third sheet (15) is further provided with its periphery bonded to the first sheet (11) to form a closed space. The force bearing the patient is measured by measuring the pressure in the space formed.

7 Claims, 8 Drawing Sheets

FOREIGN PATENT DOCUMENTS

| | | |
|---|---|---|
| JP | 2001-149185 | 6/2001 |
| JP | 2002-98601 | 4/2002 |

* cited by examiner

BEDSORE MAIN-FACTOR MEASURING DEVICE

TECHNICAL FIELD

This invention relates to an apparatus (referred to as pressure ulcer factor evaluation apparatus) for evaluating factors that may cause pressure ulcers over, for example, bed-stricken patient's back and/or buttock, and more particularly to a pressure ulcer factor evaluation apparatus for measuring the "pressure" and "shearing force" acting on the patient's skin that may cause pressure ulcers.

BACKGROUND ART

There has been known a care index called Braden scale for predicting a risk of pressure ulcer. This scale is based on the examinations and assessments of patient's physical conditions, including his sensation of pressure, wetness of skin, activeness, mobility, nutrient condition, and friction and shear occurring on his skin. The Braden scale is used to prognosticate pressure ulcers. By improving risky conditions and providing preventive measures against those factors that lead to pressure ulcer, it is possible to minimize development of pressure ulcers. Of the factors mentioned above, "friction" implies friction of an object slipping on skin by a relatively weak external. Friction is a risk factor in that it can damage the skin and become a cause of pressure ulcer. "Shear" implies compression or stretching of tissues lying between the skin and a bone occurring under a tangential stress due to a relatively strong external force acting on the skin. "Shear" is a risk factor in that it can cause blood stream inhibition leading to pressure ulcer.

As shown in FIG. 9, when the body of a patient 2 lying on a medical bed or nursing care bed, such as Gatch bed 1 whose back and knee sections can be bent (lifted), shearing forces "a" act on the patient's body in the direction from the lower half to the upper half of the body and shearing forces "b" act in the opposite direction. Such forces are generated over such regions of the patient's body as the scapula 3, lumbar 4, sacrum bone 5, and thighbones 6 during lifting up of the Gatch bed by a care worker in lifting and/or adjusting the patient's back and/or knee or moving the patient. When the patient 2 is too weak to move his body for himself, he cannot relieve himself of the shearing forces "a" and "b". If the patient were left under such condition, the shearing forces would develop pressure ulcers at bony prominences.

Unfortunately, there is no known apparatus for measuring such shearing force actually acting on the patient's skin and causing pressure ulcer. As a consequence, no satisfactory analysis of shear has been made so far. Moreover, how a shearing force acts on the patient's body depends on the patient 2. That is, it depends on the region of the body the force acts, his weight and somato type, and whether a bony prominence exists or not. Thus, these factors must be also taken into account in the analyses. Therefore, in order to make more accurate the assessment of such care index as Braden scale, a need exists for an improved apparatus capable of accurately measuring a shearing force acting on patient's body.

In view of the circumstances as mentioned above, the invention is directed to an apparatus for accurately measuring the shearing force and pressure acting on the patient's skin and calculating the resultant force arising from the shearing force and the pressure accurately to evaluate risk factors that may cause pressure ulcer.

DISCLOSURE OF INVENTION

In accordance with one aspect of the invention, there is provided an apparatus for evaluating factors that may cause pressure ulcer on, for example, a patient's back and/or buttock (the apparatus hereinafter referred to as pressure ulcer factor evaluation apparatus), comprising:

a sensor section that can intervene between the patient's body and a bed, having
  an air-filled space whose pressure can be varied by the pressure exerted by the patient's body (the pressure referred to as surface pressure and the space referred to as surface pressure measuring space) when said sensor section is inserted between said body and bed,
  an air tube hermetically connected to and communicating with the surface pressure measuring space,
  a space accommodating at least one strain gauge for measuring the shearing force acting on the patient's skin in the tangential direction of the skin (the space referred to as shearing force measuring space),
  a signal line connected to the strain gauge for transmitting the signal generated by the strain gauge out of the shearing force measuring space; and
a controller-display unit having
  a pressure sensor communicating with the surface pressure measuring space via the air tube for detecting the surface pressure transmitted from the surface pressure measuring space, and
  a display adapted to process the data received from the strain gauge and pressure sensor to obtain and display information indicative of the surface pressure (referred to as surface pressure information) and information indicative of the shearing force (referred to as shearing force information).

The sensor section is inserted between the patient and bedding, e.g. a bed. It should be understood that we mean by "between the patient's body and bedding" not only between the patient's clothes such as pajamas and sheets but also between the patient's skin and clothes. If a shearing force takes place between the patient and the bed when moving the body of the patient during care for example, the shearing force will cause the two sheets of the sensor section to be dislocated with each other or sheared, which shear will be detected by the strain gauge. At the same time, as the surface pressure measuring space is compressed by the weight of the patient to thereby increase the pressure inside, the incremental pressure will be detected by the pressure sensor. The signals received from the strain gauge and from the pressure sensor are indicated on the display as information indicative of the shearing force (tangential force) and surface pressure (normal force), respectively.

In this arrangement, the surface pressure measuring space is preferably provided therein with a sponge (urethane foam)-like spacer for securing a minimum height of the space, thereby securing a minimum amount of air in the surface pressure measuring space and preventing a measurement error due to insufficiency of air in the space.

The surface pressure information obtained by the pressure sensor and the shearing force information obtained by the strain gauge may be integrated to obtain a resultant or total force and shown as the total force information on the display. Since the total force information is shown in addition to the individual surface pressure information and the shearing force, sources of pressure ulcer can be grasped more accurately.

BEST MODE FOR CARRYING OUT THE INVENTION

Figure 1:
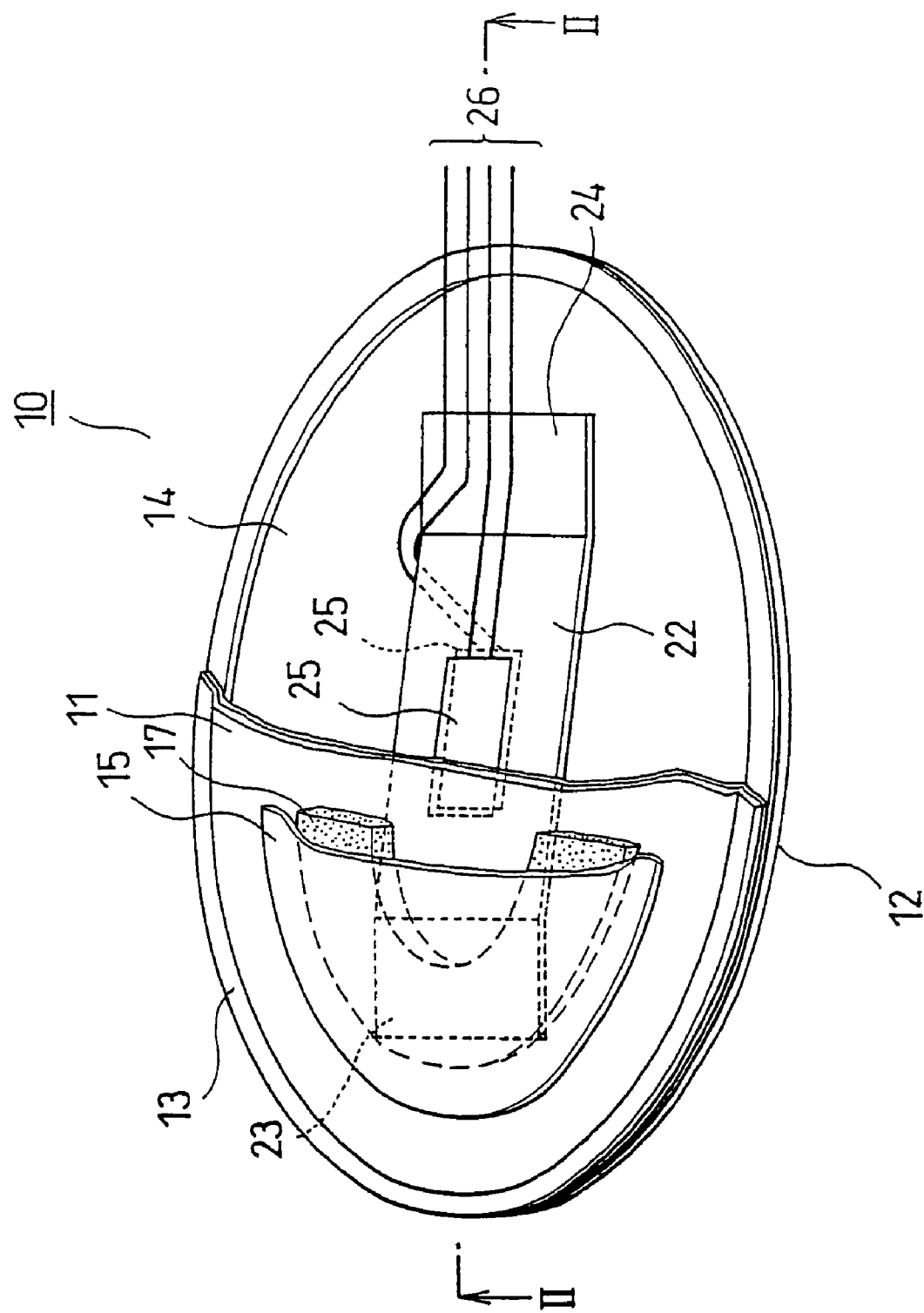
FIG. 1 is a perspective view, partly cut away, of a sensor section of the inventive pressure ulcer factor evaluation apparatus for measuring surface pressure and shearing force.
Figure 2:
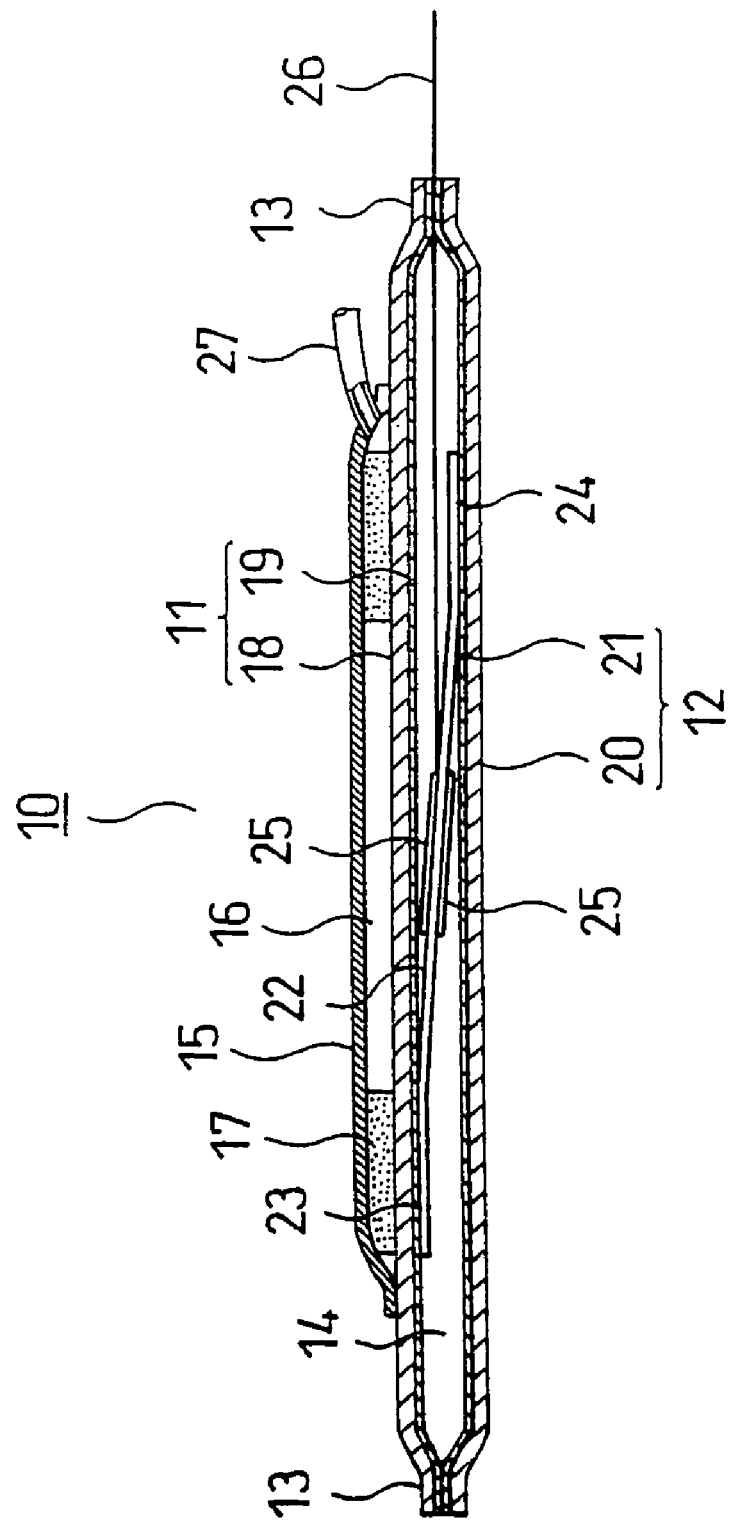
FIG. 2 is a sectional view taken on line II—II of FIG. 1.
Figure 3:
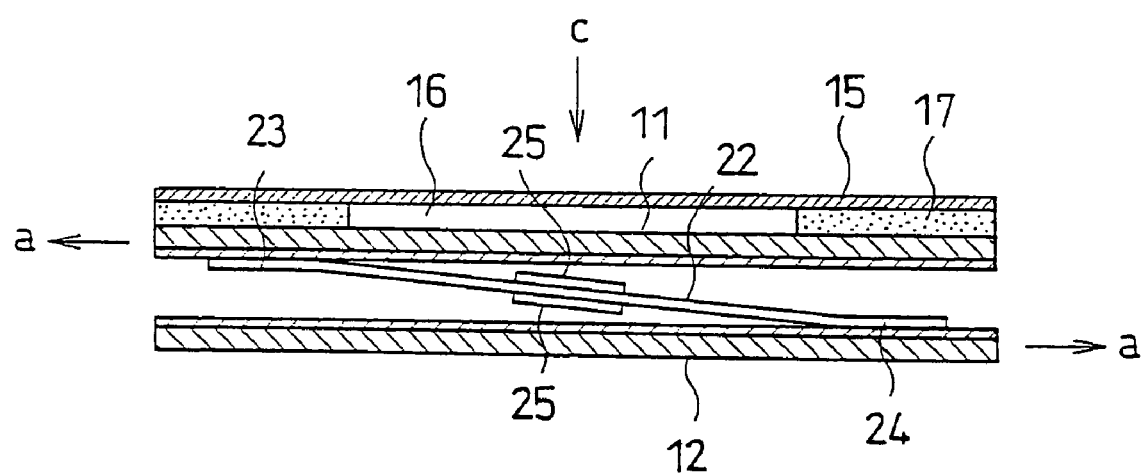
FIG. 3 is a sectional view of a main body of the pressure ulcer factor evaluation apparatus, illustrating the functions of distortion generating sheets and a strain gauge of the sensor section.

Referring now to FIGS. 1 and 2, there is shown a sensor section 10 having a first sheet 11 made of a flexible sheet and a second sheet 12 made of a flexible sheet underlying below the first sheet 11. Both sheets are circular in shape and have diameters of about 10 cm. The first and second sheets 11 and 12, respectively, have circumferential sections 13 bonded together to form inside thereof a shearing force measuring space 14. The shearing force measuring space 14 can communicate with an external unit, and hence it is not closed. In this arrangement, when a pair of shearing forces "a" are applied to the first and second sheets 11 and 12, respectively, as shown in FIG. 3, the sheets will be dislocated, or slip, with each other in the directions of the respective shearing forces.

A third flexible circular sheet 15, smaller in diameter than the first sheet 11, has a circumferential edge bonded to the first sheet 11 to form a hermetical surface pressure measuring space 16 between the first and third sheets 11 and 15, respectively. The third sheet is provided to transmit the shearing force acting on the patient's body to the first sheet 11 as accurately as possible. Mounted inside the surface pressure measuring space 16 is an annular spacer 17 made of a sponge (urethane foam)-like material to secure a minimum height of the surface pressure measuring space 16. The spacer 17 has a central circular space. In the example shown in FIGS. 1 and 2, although the third sheet 15 is shown to be bonded on the upper side of the first sheet 11, it may be alternatively bonded to the lower side of the first sheet 11 to form the surface pressure measuring space 16 on the side where the shearing force measuring space 14 is formed.

The first sheet 11 consists of a non-slippery surface layer 18 (having a large friction coefficient) and a slippery inner layer 19 (having a small friction coefficient). Specifically, the surface layer 18 may be a polyurethane sheet having a thickness in the range of about 0.3–0.5 mm, while the inner layer 19 may be a paper or TEFLON sheet. The second sheet 12 may alternatively consist of a surface layer 20 and an inner layer 21 each made of the same material as the first sheet 11. The inner layers 19 and 21 are made of paper or TEFLON sheet for the reason that they should have a minimum friction coefficient when they come into contact with the first and second sheets 11 and 12, respectively, yielding only negligible friction between them. The third sheet 15 may consist of a single polyurethane sheet similar to the surface layers 18 and 20 described above.

Since the surface layer 18 of the first sheet 11 and the third sheet 15 are allowed to be in direct contact with the patient's skin and must be movable together with the patient's skin when the patient's body is moved, the surface layer 18 of the first sheet 11 and the third sheet 15 must be made of a material having a large friction coefficient. Polyurethane is suitable for this purpose. On the other hand, the surface layer 20 of the second sheet 12 must have a friction coefficient similar to that of patient's skin, polyurethane (having a large friction coefficient) is also suitable for the surface layer 20.

A rectangular distortion generating sheet 22 has a bonding area 23 at one portion thereof, e.g. at one longitudinal end thereof (left end in the example shown in FIG. 2), which end is firmly bonded to the inner surface of the first sheet 11. The sheet 22 has another bonding area 24 at the opposite end thereof (right end in the example shown in FIG. 2), firmly bonded to the inner surface of the second sheet 12. The distortion generating sheet 22 may be a polyethylene terephthalate sheet or a nylon sheet having a thickness of about 0.1 mm. A set of two strain gauges 25, bonded to the opposing sides of the distortion generating sheet 22, are connected to the respective lead wires 26. The set of (two) strain gauges 25 can be any known gauges. The two strain gauges 25 are included in a Wheatstone bridge for its zero-point adjustment. As a consequence, bend signals of the strain gauges 25 is structurally eliminated, and only relevant signals indicative of the expansion of the distortion generating sheet 22 is extracted. An air tube 27 connects the surface pressure measuring space 16 to a pressure sensor described later.

As shown in FIG. 3, when a shearing force is applied to the first sheet 11 in tangential direction (which amounts to a tensile force to the second sheet 12 in "a" direction), the distortion generating sheet 22 is pulled to the right and left by the tensile force, creating a distortion therein, which is detected by the strain gauge 25. In the arrangement shown herein, shear or dislocation of the first sheet 11 can be detected only in one direction ("a" direction) with respect to the second sheet 12. On the other hand, when a pressure is applied in the direction "c" perpendicular to the third sheet 15 of the surface pressure measuring space 16 as shown, the pressure is detected by a pressure sensor as described later.

Because of the sponge (urethane foam)-like spacer embedded in the surface pressure measuring space to secure the minimum height of the space, a minimum amount of air is secured in the space, thereby preventing an error in the measurement of pressure due to insufficiency of air, thereby enabling accurate and stable measurement of the surface pressure.

Figure 4:
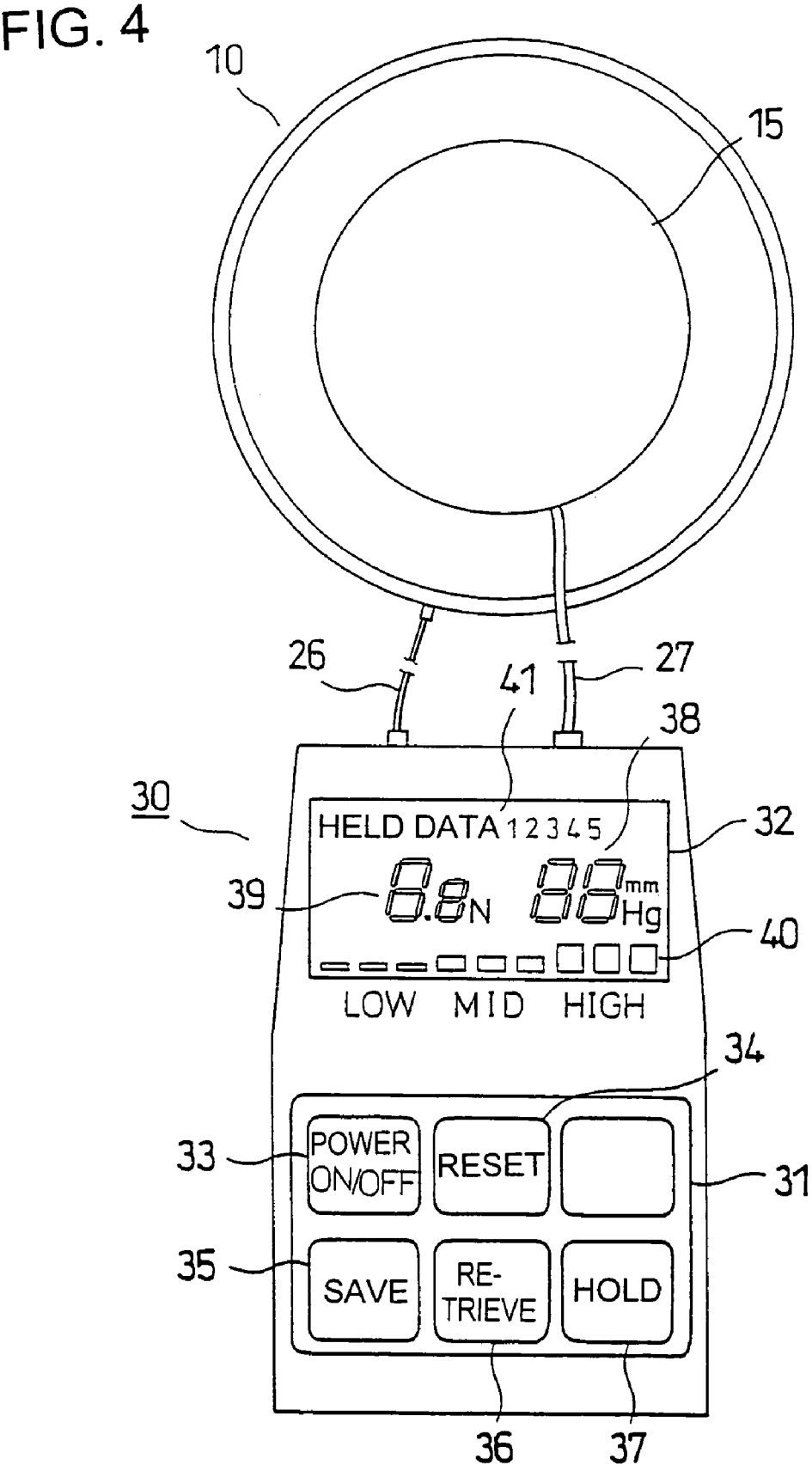
FIG. 4 is a plan view of the sensor section and a controller section of a controller-display unit.

A controller-display unit 30 shown in FIG. 4 receives signals from the sensor section 10. The controller-display unit has on the surface thereof a switch section 31 having a multiplicity of thin key-type switches and a display section 32. The key switch section 31 includes a "power on/off" switch 33, a "reset" switch 34, a "save" switch 35 for saving data, a "retrieve" switch 36 for retrieving data, and a "hold" switch 37 for holding data. The display section 32 includes a surface pressure display area 38, a shearing force display area 39, a resultant force indicator 40 for indicating the resultant force calculated from the surface pressure and shearing force, and a "held data" display 41 for displaying the data held.

Figure 5:
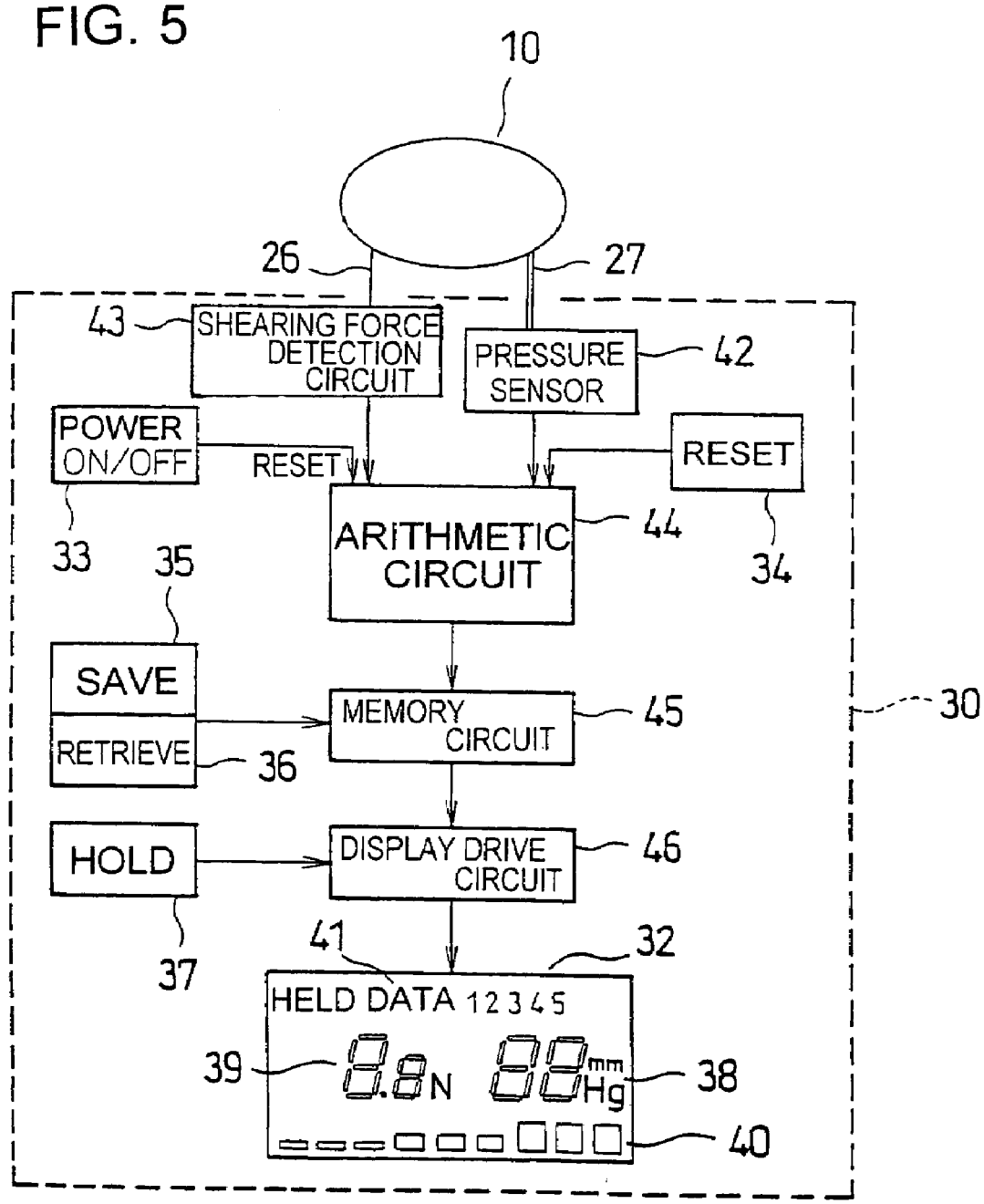
FIG. 5 shows a circuit arrangement, shown in block diagram, of the sensor section and the controller section.

The controller-display unit 30 has a structure as shown in FIG. 5, in which the surface pressure signal detected by the sensor section 10 is transmitted to a pressure sensor 42 via the air tube 27. The shearing force signals are transmitted to a shearing force detection circuit 43 via lead wires 26 where the signals are converted into an appropriate electric signals before it is supplied to an arithmetic circuit 44. The surface pressure signal is converted by an arithmetic circuit 44 into a surface pressure information signal in units of mmHg, and then sent to a memory circuit 45 for storage. The shearing force signal is converted by the arithmetic circuit 44 to a shearing force information signal in units of N (Newton), and sent to the memory circuit 45. At the same time, the surface pressure signal and shearing force signal are processed in the arithmetic circuit 44 to compute the resultant force based on the formula (1) below, and stored in the memory circuit 45. The fractional part of the resultant force is rounded and only the integral part is shown by a corresponding number of level bars.

$$\text{Number of level bars} = \qquad (1)$$

where P stands for the surface pressure information signal, and S for the shearing force information signal.

The following table shows a general relationship between the number of level bars and corresponding surface pressure information signal P and shearing force information signal S. The number of level bars listed in the table ranges from 1 to 9.

| | S[N] | | | | | | | | | |
|---|---|---|---|---|---|---|---|---|---|---|
| P[mmHg] | 0.0 | 1.0 | 2.0 | 3.0 | 4.0 | 5.0 | 6.0 | 7.0 | 8.0 | 9.0 |
| 72 | 9 | 9 | 9 | 10 | 10 | 11 | 11 | 12 | 12 | 13 |
| 64 | 8 | 8 | 8 | 9 | 9 | 9 | 10 | 11 | 11 | 12 |
| 56 | 7 | 7 | 7 | 8 | 8 | 9 | 9 | 10 | 11 | 11 |
| 48 | 6 | 6 | 6 | 7 | 7 | 8 | 8 | 9 | 10 | 11 |
| 40 | 5 | 5 | 5 | 6 | 6 | 7 | 8 | 9 | 9 | 10 |
| 32 | 4 | 4 | 4 | 5 | 6 | 6 | 7 | 8 | 9 | 10 |
| 24 | 3 | 3 | 3 | 4 | 5 | 6 | 7 | 8 | 9 | 9 |
| 16 | 2 | 2 | 2 | 3 | 4 | 5 | 6 | 7 | 8 | 9 |
| 8 | 1 | 1 | 1 | 2 | 4 | 5 | 6 | 7 | 8 | 9 |
| 0 | 0 | 1 | 1 | 1 | 4 | 5 | 6 | 7 | 8 | 9 |

The surface pressure information P and shearing force information S supplied from the memory circuit 45 to the display section 32 via a display drive circuit 46 is digitally displayed on the display areas 38 and 39, respectively, and the resultant force is indicated by multiple level bars on the resultant force indicator 40. The resultant force indicator 40 comprises three groups of level bars, each group having level bars of different lengths that correspond to different magnitudes of the force. That is, the three groups represent three levels (LOW, MID, and HIGH) of pressure ulcer risk. For example, LOW indicates the lowest level of risk, while HIGH indicates the highest level of risk. Incidentally, all the level bars are turned off if the calculated value of the resultant force is zero, while all of the nine level bars are flickered if the value is 10 or greater (which corresponds to cases for which the number is either 10, 11, 12, or 13 in the table).

In this way, in addition to the surface pressure information and shearing force information displayed in the display section 32, the resultant force information based on them is also displayed together, so that one may grasp more accurately possible risks leading to pressure ulcer.

The reset switch 34 is provided to allow the reading of the shearing force detection circuit 43 to be reset after the sensor section 10 is placed beneath the patient's body. The resetting is required to clear the reading of the shearing force generated during the insertion of the sensor section 10 and to carry out zero-point adjustment. The pressure sensor 42 is reset and its zero-point adjustment is performed simultaneously when the power switch 33 is turned on. This is to zero the reading of detected pressure when no load exists. To describe this in more detail, as the power switch 33 is turned on to activate the evaluation apparatus, the pressure sensor 42 is simultaneously reset and its zero point is adjusted. Next, the sensor section 10 is placed under the patient's body and reset by pressing the reset switch 34 for zero adjustment of shearing force detection circuit 43. Under this condition, if friction takes place subsequently between the patient's body and the bed while lifting up of the bed for example, resulting in a shear in his body, a true shearing force detection signal can be obtained from the shearing force detection circuit 43. At the same time, the pressure can be detected by the pressure sensor 42.

The save data switch 35 is provided to store data for five measurements in the memory circuit 45. The five data (first through fifth data) can be displayed in turn in accordance with the number of operations of the data retrieval switch 36. The hold switch 37 fixes the displayed value of measurement as it is. In other words, although the lowest digit of the measured value fluctuates with a short period, the hold switch 37 fixes the value of the measurement and displays a fixed value in a stable manner.

Figure 6:
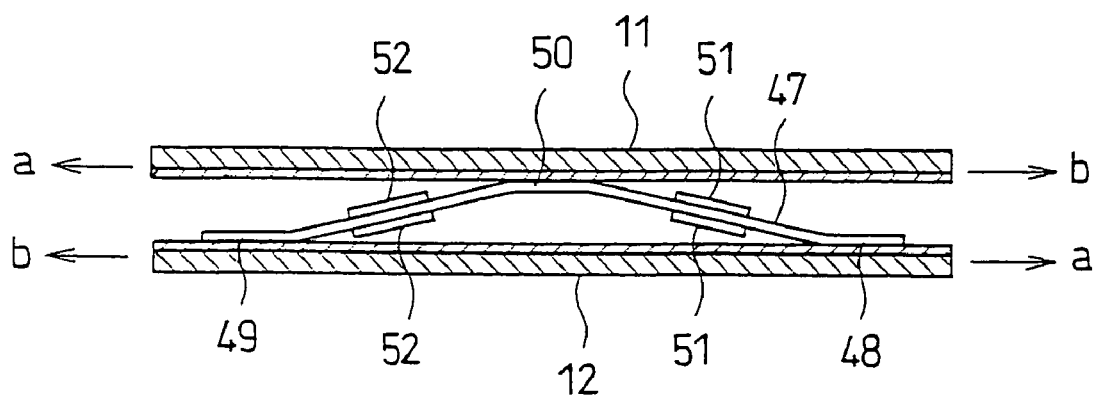
FIG. 6 is a partial sectional view of the main body of another sensor section in accordance with the invention, illustrating functions of the distortion generating sheets and strain gauges of the sensor section.

Referring to FIG. 6, there is shown another configuration of the distortion generating sheet 22, alternative to the one shown in FIG. 2. The surface pressure measuring space is not shown in FIG. 6. This sheet is adapted to detect the shear of the sheet 22, or the dislocation of the first sheet 11 in either direction (to the right or left) relative to the sheet 12. There is shown in FIG. 4 a rectangular sheet 47 having opposite longitudinal ends 48 and 49 bonded to the inner surface of the second sheet 12, and the central area 50 bonded to the first sheet 11. Bonded to the upper and lower surfaces of the distortion sheet 47 and located between the central area 50 and the longitudinal end 48 of the distortion sheet 47 are a first set of two strain gauges 51. A similar second set of strain gauges 52 are also provided between the central area 50 and the end 49 of the distortion generating sheet 47. The shearing force across the sheets 11 and 12 (due to tensile forces acting on the sheets 11 and 12) in "a" direction can be detected by the first set of the strain gauges 51, while a shearing force in "b" direction can be detected by the second set of strain gauges 52.

Figure 7:
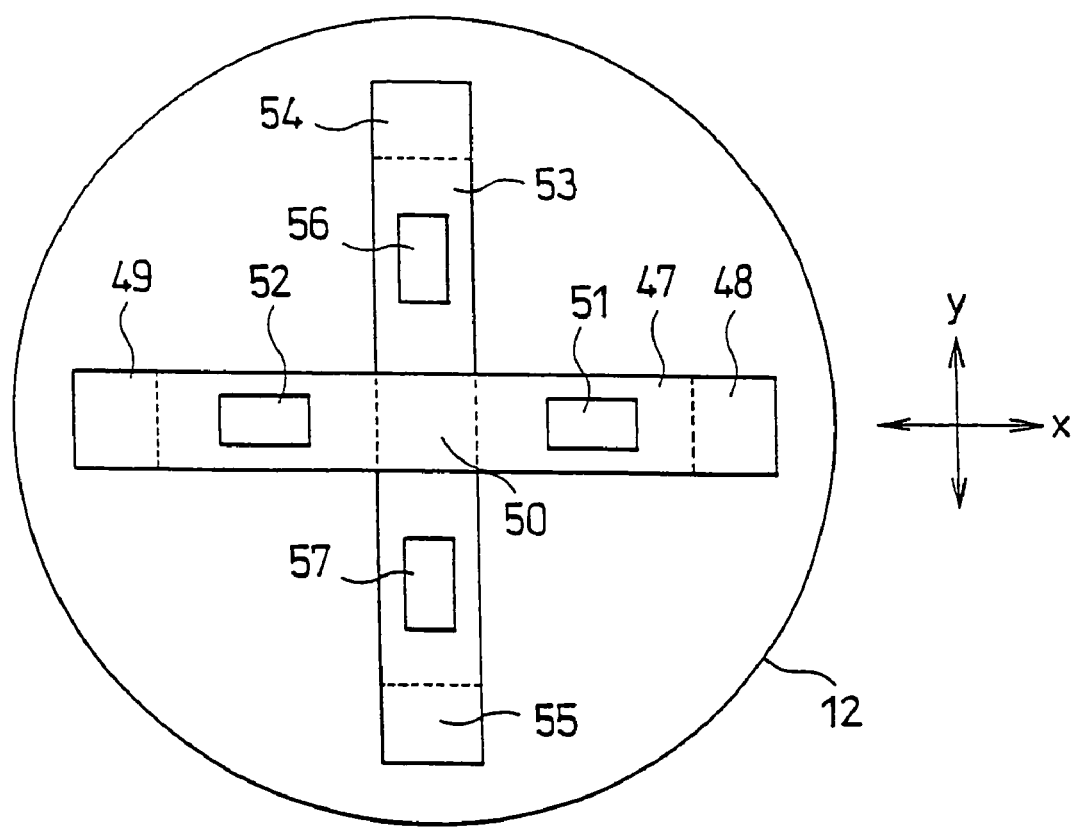
FIG. 7 is a partial sectional view of the main body of a still another sensor section in accordance with the invention, illustrating functions of the distortion generating sheets and strain gauges of the sensor section with a first and a third sheets removed.

Referring to FIG. 7, there is shown a still another distortion generating sheet adapted to detect shears in two perpendicular directions (respectively referred to as x and y directions) by means of a first distortion generating sheet 47 extending in x-direction and by a second distortion generating sheet 53 extending in y-direction. The first and second distortion generating sheets 47 and 53, respectively, have the same structure as the one shown in FIG. 6. They only differ in that they are oriented in different directions. The longitudinally opposite ends 54 and 55 of the second distortion generating sheet 53 are bonded to the inner surface of the second sheet 12, and the central area 50 of the second sheet 53 is bonded to the inner surface of the first sheet 11. The first distortion generating sheet 47 also has the same structure as that shown in FIG. 6. The second distortion generating sheet 53 has a third set of strain gauges 56 bonded to both sides of the sheet 53 and between the central area 50 and the longitudinal end 54, and a fourth set of strain gauges 57 bonded to both sides of the sheet 53 and between the central area 50 and the longitudinal end 55. The first and second sets of strain gauges 51 and 52 enable detection of shears in x-direction (both positive and negative x-directions), while the third and fourth sets of strain gauges 56 and 57 enable detection of shears in y-direction (both positive and negative y-directions).

Figure 8:
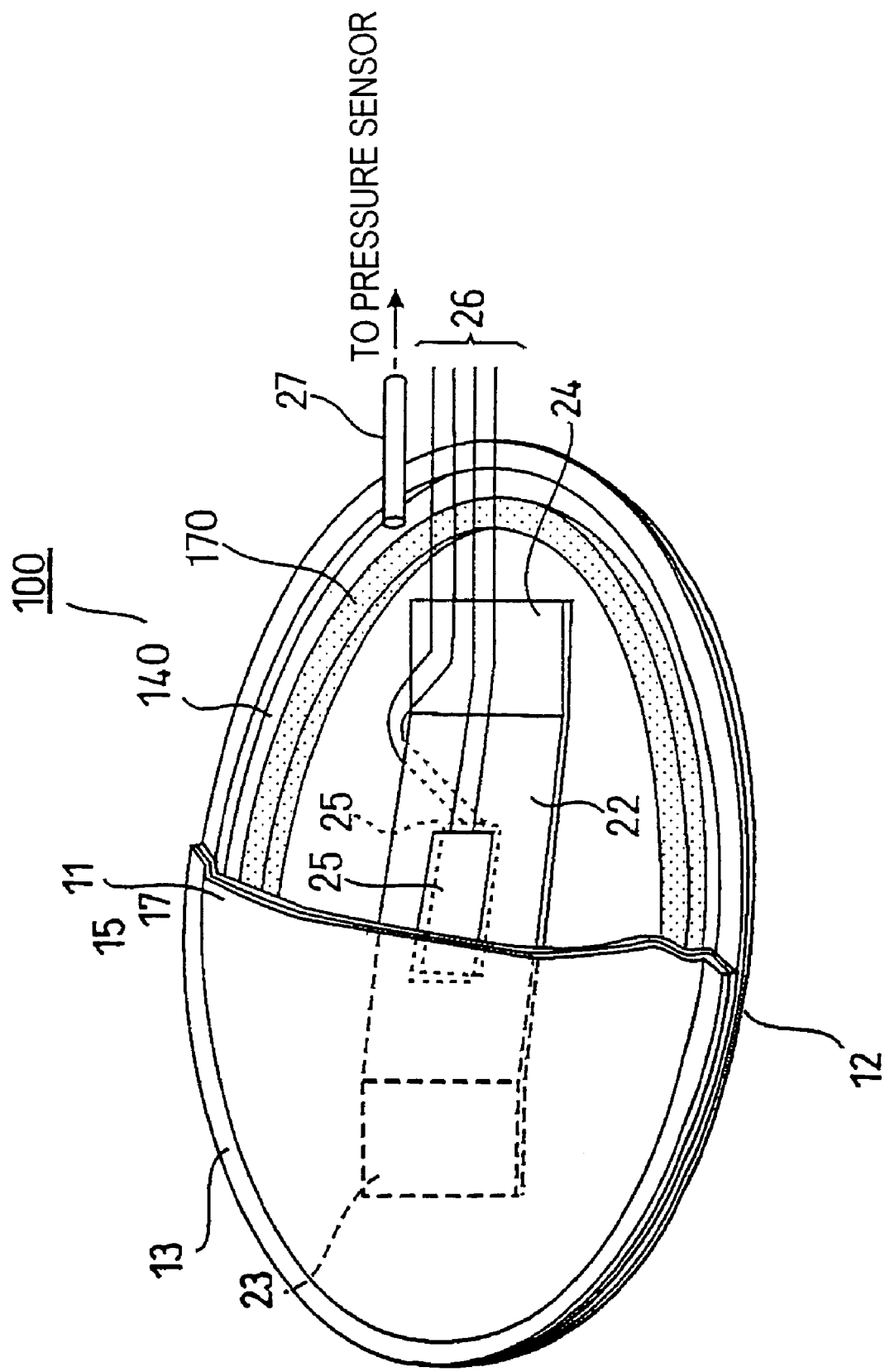
FIG. 8 is a perspective view, partially cut-away, of a further sensor section of the inventive pressure ulcer factor evaluation apparatus for measuring surface pressure and shearing force.
Figure 9:
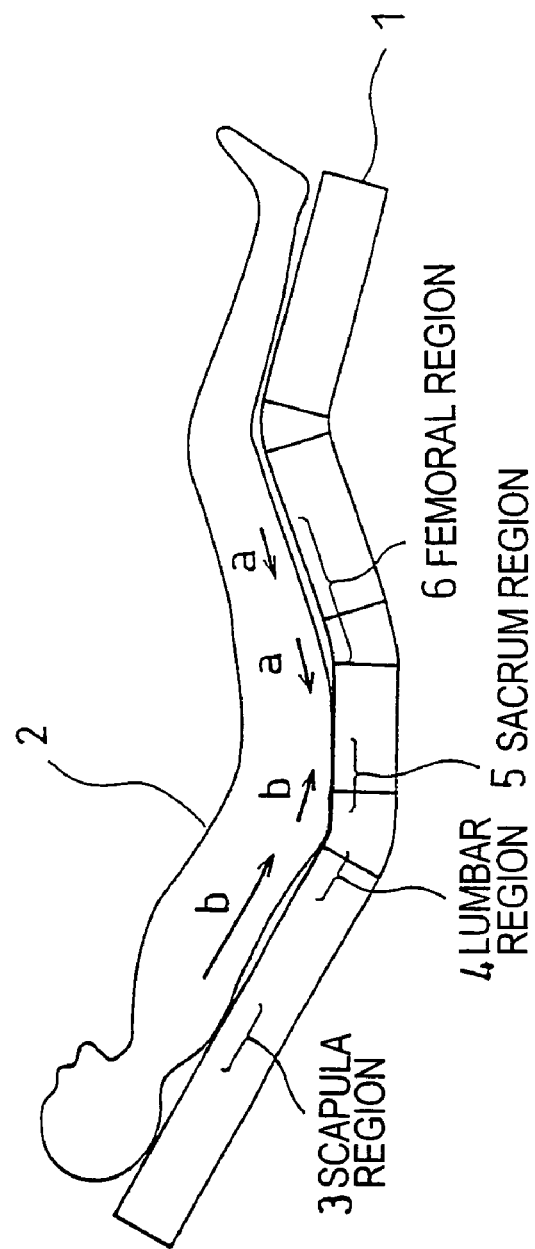
FIG. 9 is a side view of a pressure ulcer factor evaluation apparatus, illustrating how a shearing force is generated.

Referring to FIG. 8, there is shown a further surface pressure sensor section along with a further shearing force measurement sensor section of the pressure ulcer factor evaluation apparatus in accordance with the invention. It is noted that in FIGS. 1 and 8, like reference numerals indicate like components. This embodiment greatly differs in structure of FIG. 1 in that the shearing force measuring space 14 and the surface pressure measuring space 16 are integrated into a single measuring space 140.

That is, the sensor section 100 shown in FIG. 8 greatly differs from the sensor section 10 of FIG. 1 in that: first, the third sheet 15 of FIG. 1 is omitted; second, the circumferential edges 13 of the first and second sheets 11 and 12, respectively, are securely bonded to form a single measuring space 140 for hermetically enclosing a gas (air) therein, making the measuring space 140 to serve as the surface pressure measuring space connected to an air tube for transmitting the pressure inside thereof to the outside, as well as the shearing force measuring space equipped with strain gauges.

In order to keep the first sheet 11 and the second sheet 12 separated and secure a minimum volume in the measuring space 140, an annular sponge (urethane foam)-like spacer 170 is installed in the space 140. This is because a minimum amount of air in the measuring space 140 is necessary for the measurement of pressure. If the spacer 170 were not present, the first and second sheets 11 and 12 would come into contact with each other when a surface pressure were applied, making the volume extremely small and disabling the measurement of the surface pressure. In order to prevent such condition, the spacer 170 is provided to give the space 140 a minimum volume necessary for surface pressure measurement. Normally, a certain amount of air is injected into the measuring space 140 via the air tube 27 to keep the space 140 slightly inflated. Injection of air into the space 140 can be done by disconnecting the air tube 27 once from the pressure sensor 42, injecting air into the space 140 through the tube 27, and again tightly connecting the air tube 27 to the pressure sensor 42.

The distortion generating sheet 22 has at the opposite ends thereof bonding areas 23 and 24, which are bonded to the respective inner surfaces of the first sheet 11 and the second sheet 12. Strain gauges 25 are firmly bonded to both sides of the distortion generating sheet 22. Lead wires 26 connected to the strain gauges 25 is allowed to extend out of the measuring space 140 through the circumferential edge 13 while keeping the space 140 hermetically sealed. The air tube 27 is also extended from the circumferential edge 13 to the pressure sensor 42, keeping the space 140 hermetically sealed.

In the arrangement shown, the surface pressure applied to the sensor section 100 is transmitted to the pressure sensor 42 via the air tube 27, and converted to a surface pressure signal, which is imputed to the arithmetic circuit 44. The shearing force acting on the patient's skin is transmitted to the distortion generating sheet 22 and detected by the strain gauges 25. The signals generated by the strain gauges 25 are supplied to the shearing force detection circuit 43 via the lead wires 26, from which circuit 43 a signal (referred to as shearing force signal) is supplied to the arithmetic circuit 44. Subsequent procedures for processing signals is the same as that described above in the foregoing examples.

The sensor section 100 configured in this manner is more compact in form and cost-effective as compared with the foregoing examples.

INDUSTRIAL APPLICABILITY

According to the invention, both perpendicular force (or surface pressure) and tangential shearing force acting on the patient's skin are simultaneously measured by a sensor section inserted between the patient's body and the bedding, e.g. a bed. These forces are displayed on a display, from which one may conduct a wide range of analyses including determination of: a surface pressure and a shearing force acting on a particular region of the patient's body such as sacrum region and lumber region; the difference in surface pressure and in shearing force due to a bony prominence; and the relationship between a pressure ulcer created and the associated surface pressure and/or shearing force. Thus, the invention enables collecting data necessary to establish an effective measure to suppress pressure ulcers.

The invention claimed is:

1. A pressure ulcer factor evaluation apparatus for evaluating factors that may cause pressure ulcer on a patient's back and/or buttock, said pressure ulcer factor evaluation apparatus comprising:
   a sensor section that can intervene between the patient's body and a bed, having
      an air-filled surface pressure measuring space whose pressure can be varied by the surface pressure exerted by the patient's body when said sensor section is inserted between said body and bed,
      an air tube hermetically communicating with said surface pressure measuring space,
      a shearing force measuring space accommodating at least one strain gauge for measuring the shearing force acting on the patient's skin in the tangential direction of the skin,
      a signal line connected to said strain gauge for transmitting the signal generated by said strain gauge out of said shearing force measuring space; and
   a controller-display unit having
      a pressure sensor communicating with said surface pressure measuring space via said air tube for detecting the surface pressure transmitted from said surface pressure measuring space, and
      a display adapted to process the data received from said strain gauge and pressure sensor to obtain and display bodily force information indicative of said surface pressure and shearing force information indicative of said shearing force.

2. The apparatus according to claim 1, wherein
   said surface pressure measuring space is formed of two flexible sheets hermetically bonded together along the peripheries thereof to form a closed space therebetween for enclosing an amount of air;
   each of said distortion generating sheets is provided on the inner surface thereof with said strain gauge and is fixed at the opposite ends thereof to the inner surface of corresponding one of said two flexible sheets, whereby said surface pressure measuring space is adapted to also serve as said shearing force measuring space.

3. The apparatus according to claim 1, wherein said shearing force measuring space is formed inside two flexible sheets hermetically bonded together along the peripheries thereof, with each of said two sheets provided on the inner surface thereof with a distortion generating sheet having opposite ends fixed to said inner surface, and each of said distortion generation sheet provided on at least one surface thereof with a strain gauge, and wherein said surface pressure measuring space is formed inside a third sheet and one of said two sheets, with said third sheet bonded along the periphery thereof to said one of two sheets, and said surface pressure measuring space inflated with an amount of air.

4. The apparatus according to claim 2 or claim 3, wherein each of said distortion generating sheets having thereon at least one strain gauge, is fixed at the opposite ends thereof to said inner surface of said sheet such that said distortion sheet is oriented in the direction preferred to measure shearing force.

5. The apparatus according to claim 4, wherein said two flexible sheets are provided on the inner surfaces thereof with a multiplicity of distortion generating sheets.

6. The apparatus according to claim 1, 2, or 3, wherein said surface pressure measuring space accommodates a sponge-like spacer for securing a minimum height of said space.

7. The apparatus according to claim 1, wherein said display has an arithmetic circuit for calculating the resultant force that arises from said surface pressure and shearing force, based on said surface pressure information and shearing force information, and wherein said resultant force is displayed on said display.

* * * * *